| United States Patent [19] | [11] Patent Number: 4,986,981 |
| Glace et al. | [45] Date of Patent: Jan. 22, 1991 |

[54] TOOTHPASTE HAVING LOW ABRASION

[75] Inventors: William R. Glace, Orcutt; Robert L. Ibsen, Santa Maria, both of Calif.

[73] Assignee: Den Mat Corporation, Santa Maria, Calif.

[21] Appl. No.: 379,010

[22] Filed: Jul. 12, 1989

Related U.S. Application Data

[63] Continuation-in-part of Ser. No. 268,583, Jul. 7, 1986, abandoned, which is a continuation of Ser. No. 882,185, Jul. 7, 1986, abandoned.

[51] Int. Cl.$^5$ .......................... A61K 7/16; A61K 7/28
[52] U.S. Cl. ........................ 424/50; 424/49; 424/52; 424/57; 424/55
[58] Field of Search ................ 424/49, 50, 55, 57, 424/52

[56] References Cited

U.S. PATENT DOCUMENTS 3,228,844  1/1966  Strean .................................... 424/50
4,152,418  5/1979  Pader .................................... 424/50

FOREIGN PATENT DOCUMENTS 0959764  12/1974  Canada .
0095871  12/1983  European Pat. Off. .

OTHER PUBLICATIONS

Jefopoulos, *Dentifrices*, Noyes Data Corp., N.J., U.S.A., 1970, pp. 46–51.

*Primary Examiner*—F. T. Moezie
*Attorney, Agent, or Firm*—Owen, Sickersham & Erickson

[57] ABSTRACT

A toothpaste characterized by a low abrasion, non-reactive base formulation. The toothpaste has a near neutral or neutral pH. The toothpaste contains a concentration of citric acid, sodium or potassium citrate, papain, and fine-particle-sized aluminum oxide, in particular portions which effectively clean away plaque, mucin and tartar.

9 Claims, No Drawings

TOOTHPASTE HAVING LOW ABRASION

REFERENCE TO RELATED APPLICATION

This application is a continuation-in-part of application Ser. No. 268,583, now abandoned which was a continuation of application Ser. No. 882,185 filed Jul. 7, 1986, now abandoned.

This invention relates to an improved toothpaste which removes both plaque and tartar, and also prevents their accumulation. Moreover, it is not so abrasive as to adversely affect either natural teeth or dental restorations.

BACKGROUND OF THE INVENTION

Toothpastes, heretofore, have primarily been used in conjunction with brushing to remove food particles from the mouth. They have not been effective in preventing the formation of plaque; much less have they removed either plaque or tarter. Often they have tended to damage dental restorations, and in some cases even the natural teeth, or to roughen the surface, resulting in adherence of stains from coffee and tea.

Plaque is a soft sticky film that tends to coat the teeth. Living and dead bacteria or bacterial flora, and especially mucopolysaccharides comprise the plaque. It may also include various bacterial by-products, some of which are irritating toxins. If sufficient plaque accumulates on teeth and goes down into the crevices between the teeth and the gums, gingivitis may result, and the gums may become swollen and inflamed and tend to bleed easily. If the gums are neglected, periodontitis may develop. As plaque continues to grow between the gums, destroying the periodontal fibers that connect teeth to the bone, it causes pockets where more plaque collects. As periodontal disease progresses, an increasing amount of bone and tissue supporting the teeth are destroyed, and the teeth themselves may be lost, due to lack of support. The bone is lost because of the infection process in the pockets.

Plaque in its initial stages may be kept somewhat under control by prolonged and frequent brushing with ordinary toothpastes, do nothing to get rid of the accumulated plaque, and reliance has had to be made on supplementing toothbrushing with flossing programs. Moreover, plaque, though barely if at all visible by itself, collects stains from foods, some alcoholic beverages, and tobacco, that make the teeth look very badly stained.

As the plaque continues to accumulate, it may combine with minerals, particularly calcium, in the saliva to form tartar. Tartar is quite different from plaque, though it has sometimes been called a calcified plaque. Dentists call it calculus. Tartar or calculus is rock hard, is a white or yellowish deposit that, once it attaches itself to the teeth, could heretofore only be removed by scaling it from the teeth and from under the gums during professional cleaning. Tartar is largely inert, but controlling tartar also helps to reduce the amount of cleaning that a dentist need do. And below the gum line the accumulation of tartar may accelerate the progress of periodontal disease, by starting a foreign body reaction in which the body uses the inflammation process to expel the foreign body, which it cannot do since the root is attached to the cementum and the tartar is attached to the root.

Up to now, the main attack on plaque has been the mechanical actions of flossing and brushing, and neither brushing nor flossing has acted to remove calculus.

Recently, some anti-tartar toothpastes have been placed on the market, but these do not even purport to remove what tartar is already there; they claim merely to prevent (to some degree) the build-up of further tartar. Such tartar-inhibiting toothpastes may reduce the accumulation of new tartar by about one-third or more, but that is about the limit of their effectiveness.

In the past some toothpastes made attempts to control plaque by abrasion, but the attempts were unsuccessful or led to very bad side effects. For example, some toothpastes in the past contained strong acids which acted very well to whiten teeth, but ruined the tooth enamel. Actually they were not very effective in the control of tartar or plaque.

Among the objects of the present invention are the control and removal of plaque and tartar. Regular and thorough brushing with the toothpaste of the present invention will prevent—either wholly or to a large degree—the accumulation of plaque and the formation of tartar.

At the same time an object of this invention is to avoid the problem of tooth damage that prior attempts for controlling plaque and tartar have caused. Not only are the natural teeth not damaged, even dental restorations, which are softer than teeth, are not damaged. The abrasive action in the preferred forms of this toothpaste, are sufficiently controlled so that they do not scratch the teeth nor even dental restorations.

When tooth-colored, glass-filled polymers are used for the filling of cavities in anterior teeth and then are polished to a lustrous finish that can be evaluated as smooth, they become clinically stain resistant. Unfortunately, the use of prior art toothpastes on tooth-colored plastic has tended to roughen the surface and leave the surface more prone to picking up stains.

The toothpaste of the present invention has been shown in actual tests to have left the tooth-colored plastic surface not significantly different from that of a professionally polished lustrous surface of the tooth colored polymer plastic. Therefore, it helps the tooth prevent the deposit of stains from food, drinks, and smoking, as well as tending to remove them.

Thus, an important object of this invention is to provide an improved toothpaste that attacks plaque and tartar selectively and can remove plaque and tartar from tooth structure without causing unnecessary wear on the existing tooth structure, that is, the enamel, the dentin, and the cementum.

Another object is to remove stain from the accessible surfaces of teeth without scratching the teeth. In fact, the abrasivity of this improved toothpaste is typically less than that of a smoker's toothpaste, using the American Dental Association abrasivity index on tooth dentin surfaces. It is also less abrasive on tooth colored filled polymer dental restoratives than are the current dental prophylaxis pastes.

Another important feature of the invention is to maintain an acid-base neutrality in the toothpaste, so that the toothpaste has a pH of approximately 7.

SUMMARY OF THE INVENTION

A main feature of the present invention is its incorporation of sodium or potassium citrate and preferably, citric acid to aid in preventing the formation of and causing the removal of plaque and calculus. These ingredients provide no abrasive action, and are preferably used in such proportions as to achieve a substantially neutral if not actually neutral pH. The use of citric acid is not absolutely vital, but is a very useful agent in adjusting the pH. Without the citric acid, the pH of the citrate tends to be about 8.5, and the citric acid can be used in small amount to maintain a pH close to or actually at 7.0.

Preferably, papain is used in conjunction with the alkali-metal citrate-citric acid combination. Papain, as used herein, refers to the crystalline proteolytic enzyme rather than the crude dried latex. It is a preparation form commercial dried papaya latex. According to the Merck Index, the papain molecule consists of one folded polypeptide chain of 212 residues with a molecular weight of about 23,400. It is practically insoluble in most organic solvents, but is somewhat soluble in water or glycerine. Even when used without the citrate, papain has a tendency to dissolve and remove plaque. It is believed that this proteolytic enzyme serves to dissolve the proteinaceous matrix of calculus that is attached to dentin and enamel. However, papain, when used without the citric acid combination, has no effect whatever on the calcium content of calculus. When used in conjunction with the citrate/citric acid combination, however, it is able to add to the effectiveness of that material. As a result of the action of the citrate or citric acid, the papain can penetrate through the calcium-compounds to get at the proteinaceous materials. Thereby, it is much more effective than it would be alone. Moreover, it appears to enhance the effect of the citrate ions on the plaque as well as on the calculus.

The alkali-metal citrate, the citric acid, and the papain (in quantities that will be later described) can be added to practically any typical or ordinary toothpaste and will provide desired results.

Most commercial toothpastes are made up of seven major types of ingredients; namely, (1) an abrasive material, (2) a humectant or moistening system, (3) a thixotropic agent or binder to help hold the ingredients together, (4) water, (5) a flavoring mixture, (6) a foaming agent, usually a synthetic detergent, and (7) a low level of preservative.

The citric-acid sodium (or potassium) citrate and papain employed in this invention may be used in conjunction with just such a toothpaste.

Preferably, the present invention, in addition to employing ordinary abrasives, uses a certain amount of small-particle-size aluminum oxide, either hydrated or nonhydrated, but of a type which is small enough in particle size so that there is no scratching of the teeth of dental restorations. The aluminum oxide may be used in conjunction with the typical water insoluble, paste adapted, abrasives used in dentifrices.

(1) The abrasive of the toothpaste may be dicalcium phosphate, insoluble sodium metaphosphate, calcium pyrophosphate, calcium orthophosphate, calcium carbonate, magnesium carbonate, or one of a variety of silicates and dehydrated silica gels. Since these agents can differ in their degree of abrasiveness, both between the various types and within each type itself, the abrasiveness is carefully observed and is adjusted to a proper amount which tends to polish teeth, but not to scratch them, whether the teeth are natural teeth, or restorations.

(2) Humectants are employed to prevent loss of water from the toothpaste when it is exposed to air. The most frequently such used humectants are sorbitol, glycerin and propylene glycol. Sorbitol and glycerine tend to have a sweet taste.

(3) Thixotropic agents or binders help to stabilize the dentifrice formulation and prevent separation of the liquid from the solid phases. A number of agents having hydrophilic colloidal properties are used, such as natural gums, including gum traganth and gum karaya. The seaweed colloids such as various carageenans, extracts of Irish moss, and sodium alginate are used. Synthetic celluloses including sodium carboxymethyl cellulose and methyl cellulose are used, and mineral colloids such as bentonite have been used. These materials are not essential by any means to the present invention, but may be used along with it.

(4) Water is used in order to have the paste in a smooth, flowable form.

(5) Flavoring agents used in dentifrices are of a wide variety, but have nothing to do with the cleaning, except that the pleasantness of the flavors, at lease does not repel people from longer brushing. Cinnamon and mint are among the most popular flavors.

(6) Foaming agents are often added to toothpastes, but serve mainly to give a pleasant sensation, and apparently serve little or no cleaning purpose. Sodium lauryl sulfate, the one presently most frequently used, has generally replaced soap because there fewer compatibility problems in combining it with the other ingredients.

(7) Sometimes preservative is added to prevent bacteria from forming in the toothpaste itself. This again is not an essential ingredient, but is one that is often desirable.

In addition, such things as coloring agents may also be used.

The abrasive may comprise about 40–60%, by weight, of the total bulk of a toothpaste suitable for the present invention. Water may comprise about 11–15% by weight and humectant, using one or more of them, may comprise between about 20–30% by weight of the whole.

A foaming agent, if used, preferably comprises less than 1% and may be about 0.7–0.9%, while the thixotropic agent is in slightly less amount, 0.6–0.8%, both by weight.

The amount of flavoring depends on the strength of the flavoring agent; for instance, in the present invention spearmint flavor may be used in the amount of about 0.7–0.9%, by weight.

A fluoridating agent may be incorporated, if desired, without harm to the other ingredients. The fluoridating agent may be, for example, sodium monofluorophosphate in an amount of about 0.6–0.8%, by weight. Other typical amounts of other fluorides may be used if any is used at all. It will have the same effect as fluorides have in other toothpastes when used, but will not affect at all the action on plaque, tartar or polishing.

Typically, the present invention incorporates sodium citrate in an amount of between about 1–3% of the total weight of the toothpaste or potassium citrate in an amount of between 1.1% and 3.3% thereof. Citric acid may be used in combination therewith to about 3% by weight, although normally somewhat less is used. It is used in an amount to adjust the pH somewhere between about 6 and about 7.5, all in view of the other ingredients contained. An approximation of 7.0 for the pH of the completed paste is desirable.

If papain is used (and it is preferably used), it may be incorporated in the amount of about 1 to about 4.5%. The papain we have used has, as determined by the Milk Clot Assay Test of the Biddle-Sawyer Group, an activity of 100-145 units per milligram. (See J. Biol. Chem., Volume 121, pages 737-745, (1937)). If papain, having a different activity, were to be used, it would be adjusted in an amount to correspond.

If the abrasive is of the typical types, it may be wise to incorporate aluminum oxide of very small particle size, for instance, an average of about 1 micron in an amount of 4-12% of the weight in addition to the 40-50% by weight of a main abrasive. Thus, a typical formulation of the toothpaste of this invention may be:

TABLE 1

Typical Formulation of a Toothpaste of this Invention

| Ingredients | Percent by Weight |
|---|---|
| Abrasive (e.g., dicalcium phosphate) | 40-50 |
| Water | 11½-14½ |
| Humectant (e.g., mixture of sorbitol and glycerine) | 20-30 |
| Thixotropic Agent (e.g., sodium carrageenan) | 0.6-0.8 |
| Foaming Agent (e.g., sodium lauryl sulfate) | 0.7-0.9 |
| Flavor (e.g., Spearmint) | 0.7-1.0 |
| Sweetener (e.g., sodium saccharin) | 0.09-0.11 |
| Fluoride source (e.g., sodium monofluorophosphate) | 0.6-0.8 |
| Biocide (e.g., methyl paraben) | 0.06-0.08 |
| Color (e.g., FD & C Blue #1) | about 0.02 |
| Sodium citrate | 1.0-3 |
| (or potassium citrate) | 1.1-3.3 |
| Citric acid | 0-3 |
| Papain | 1-4.5 |
| Aluminum oxide (1 micron) | 4-12 |

The paste will have a pH of about 6-7.5, preferably 7.00.

The aluminum oxide may be hydrated or non-hydrated.

The papain we have used has, as determined by the Milk Clot Assay Test of the Biddle-Sawyer Group, an activity of 100-143 units per milligram.

DESCRIPTION OF SOME PREFERRED EMBODIMENTS

EXAMPLE 1

A Preferred Toothpaste of this Invention

A proven formula according to this invention is:

| Ingredients | Percent by Weight |
|---|---|
| Dicalcium phosphate | 45.22 |
| Water | 13.22 |
| Sorbital | 12.08 |
| Glycerin | 13.66 |
| Sodium carrageenan | 0.73 |
| sodium lauryl sulfate | 0.82 |
| Flavor (e.g., Spearmint) | 0.82 |
| Sweetener (e.g., sodium saccharin) | 0.11 |
| sodium monofluorophosphate | 0.73 |
| Methyl paraben | 0.07 |
| FD & C Blue #5 | 0.02 |
| Sodium citrate | 2.63 |
| Citric acid | 0.05 |
| Papain | 2.69 |
| Aluminum oxide (1 micron) | 7.16 |
| | 100.00 |

EXAMPLE 2

Testing the Tartar Removal Ability of the Toothpaste

Thirty extracted teeth were obtained from a large dental school. Fifteen had very little tartar, and fifteen had a large amount of tartar thereon. Those with little tartar were meticulously cleaned with a gold knife followed by flour of pumice. They were then designated as a "no-tartar group". Other teeth were designated as a "heavy tartar" group.

All teeth were dried of any residual moisture by exposing them to the drying lamp of an Ohaus Moisture Balance for five minutes.

The teeth were then divided into six groups, three groups were of "no tartar" teeth, and three groups were of "heavy tartar" teeth. Each group contained five teeth and was weighed as a group.

Three slurries of water and the toothpaste of Example 1 above were prepared at ratios of:
(1) 1:1
(2) 2:1
(3) 1/2:1

On of each group was submerged in a beaker of each slurry. After overnight soaking, these teeth were rinsed under a strong stream of water, re-dried under the moisture balance lamp, and reweighed as a group. Results were as follows:

TABLE II

Results of Soaking Teeth in Three Slurries of Water and the Toothpaste of this Invention

| Slurry No. | Weight Before | Weight After | Weight Change |
|---|---|---|---|
| I - Teeth with Heavy Tartar | | | |
| 1 | 8.2547 gm | 8.2394 gm | −0.0153 gm |
| 2 | 7.3169 | 7.2872 | −0.0297 |
| 3 | 8.5510 | 8.5326 | −0.0184 |
| II - Teeth with No Tartar | | | |
| 1 | 6.7535 gm | 6.7589 gm | +0.0054 gm |
| 2 | 6.8470 | 6.8508 | +0.0038 |
| 3 | 6.4669 | 6.4739 | +0.0035 |

Since each of the groups of the teeth with "no tartar" experienced a slight increase in weight, apparently due to water absorption, and each of the groups of "heavy tartar" teeth experienced a weight loss of an order of magnitude greater than the weight gain in the other group, it can be concluded that:

(1) The toothpaste of this invention attacks and removes tartar.

(2) The toothpaste of this invention does not attack tooth structure.

EXAMPLE 3

Comparison of the Toothpaste of this Invention with a Known Tartar Control Toothpaste Fifteen very dirty extracted human teeth were obtained, randomized, and separated into three groups. Each tooth was brushed on either the labial (or buccal) surface or on the lingual surface, whichever appeared dirtier and/or contained the most plaque and/or tartar. Each was brushed a total of 50 strokes with an Oral B toothbrush according to the following schedule:

Group I—Brushed with water only
Group II—Brushed with water and a commercially available tartar control formula (1:1)
Group III—Brushed with water and the toothpaste of this invention (1:1) (per Example 1)

After brushing, the teeth were water-rinsed and allowed to air-dry. When dry, each group of teeth was carefully inspected. Differences were very obvious, and were as follows:

Group I—Still very dirty. Little or no difference was seen between brushed and unbrushed surfaces.

Group II—Still very dirty. Some difference between brushed and unbrushed surfaces were apparent but not much. Some plaque and/or tartar seems to have been removed, but not much.

Group III—Brushed surfaces noticeably cleaner. Noticeably less plaque and tartar deposits remained on the teeth.

This experiment showed dramatically that the toothpaste of this invention gave considerable improvement over one of the best-known current state-of-the-art toothpastes.

EXAMPLE 4

Stain Removal Evaluation

The purpose of this study was to compare the ability of two dentifrices to remove pellicle stain from pre-stained bovine specimens. The stain in this study was developed using the usual staining procedure (coffee and tea).

Toothpaste "A" was a toothpaste similar to the toothpaste of Example 1 in all ways except that (a) it contained no citric acid, sodium citrate, or papain, and (b) it contained no aluminum oxide.

Toothpaste "B" was that of Example 1, without change.

The test groups were as follows:

| Group | Dentrifices |
|---|---|
| 1 | Sample Toothpaste A |
| 2 | Toothpaste B (Example 1) |

Specimen Preparation

Bovine permanent central incisors were cut to obtain labial enamel specimens approximately 10 mm$^2$. The enamel specimens were embedded in an autopolymerizing methacrylate resin, so that only the enamel surfaces were exposed. The enamel surfaces were then smoothed and polished on a lapidary wheel. They were lightly etched to expedite stain accumulation and adherence.

The specimens were placed on a rotating rod in a 37° C. incubator, alternately exposing them to air and to a solution consisting of trypticase soy broth, tea, coffee, mucin, FeCl$_3$, and *sarcina lutea, turtox*.

The staining broth was changed and specimens rinsed once daily for four days. After four days, a darkly-stained pellicle film was apparent on the enamel surfaces. The specimens were rinsed, were allowed to air dry, and were refrigerated until use. All products were tested using specimens prepared at the same time.

Scoring and Set-Up

The amount of in-vitro stain was graded photometrically. Specimens with scores between 15-21 (15 being more darkly stained) were used. On the basis of these scores, the specimens were divided and balanced into two groups of sixteen specimens each, with each group having the same average baseline score.

Test Procedure

The specimens were mounted on a V-8 mechanical cross-brushing machine equipped with a soft nylon-filament (Oral B 40) toothbrushes. Tension on the enamel surface was adjusted to 150 g. The dentifrices were tested as slurries consisting of 25 grams of dentifrice mixed with 40 ml. of deionized water. Specimens were brushed for 800 strokes (4½ minutes). To minimize mechanical variables, two specimens per group were brushed on each of the eight brushing heads. Four different slurries of each dentifrice were used on each run, and a single slurry was used to brush four specimens.

Following brushing, the specimens were rinsed, blotted dry, and scored again for stain as previously described.

The difference between the pre- and post-brushing stain scores was calculated and the mean standard error determined for each group. The results are tabulated in Table III below:

TABLE III

| Comparison of the Stain-Removing Ability of Two Toothpastes | |
|---|---|
| Dentrifice | Decrement |
| SAMPLE TOOTHPASTE A (like Toothpaste B, but without sodium citrate, citric acid and papain) | 6.76 ± 0.92 |
| TOOTHPASTE B (Example 1) | 12.54 ± 1.53* |

*Mean ± S.E.M. The values are significantly different (p <0.05) as determined by a student t-analysis.

The data indicate that Toothpaste B (Example 1) is significantly more effective in removing stained pellicle than Sample Toothpaste A.

EXAMPLE 5

Evaluation of Dentifrice Abrasivity

A method was developed for subjecting a small surface area to a reproducible brushing action which simulates the effect of abrasive wear induced by toothbrushing. With this method, several dentifrices can be compared on the same specimen surface, holding all other factors constant.

Using this brushing technique, four abrasive media (water as a control and three dentifrices) were tested with human dentin as the test surface. The dentin specimens were photographed at two magnifications in a scanning electron microscope. They were also prepared and submitted for microprofilometry analysis. The photographs were taken using an oblique viewing angle, in a balanced, randomized fashion at arbitrarily determined locations on the brushed surfaces. They were then ranked for surface roughness according to a three-point rating scale using a forced-choice, double-blind procedure. Correlation analysis, analysis of variance, and student-Newman-Keuls analyses were performed on the data in order to determine the statistical significance of the results.

The subjective ranking for roughness gave the following results for dentin surfaces:

TABLE IV

| Roughness Development Compared to A.D.A. Abrasivity Index of Dentifrices | | | |
|---|---|---|---|
| | Roughness | | Reported ADA |
| Brushing Medium | Scale rating* (+S.E.) | Normalized Ranking** | abrasivity index |
| Brand Y | 1.83 + 0.05 | 92 | 202 |
| Toothpaste of Example 1 in this application | 1.56 + 0.06 | 78 | — |
| Brand X | 1.12 + 0.04 | 56 | 51 |
| Water | 0 | 0 | 0 |

*2 = highest rating for roughening, 0 = smooth, non-roughened surface
**Rating scale converted to a percentage of maximum roughness rating of 2.

The differences among the roughness scale ratings and the relative order of ranking are all significant at the p<0.01 (99% probability) level.

These results rely on the integrating ability of the human eye to determine relative roughness. Therefore, they are not quantitative values. It is seen, however, that the relative ranking of the controls is in the same order as the reported ADA abrasivity indexes for these dentifrices. FIt is well known that larger abrasive particles produce greater surface roughness, and that roughness is directly related to the rapidity of abrasive wear. Therefore, the above results indicate that applicant's toothpaste produces a somewhat rougher surface and is probably more abrasive than BRAND X. On the other hand, it produces a smoother surface and is probably less abrasive than BRAND Y, a smoker's toothpaste. Profilometry results may enable quantification of these results.

BRAND W, a widely advertised smoker's stain-removing toothpaste, and BRAND Z, were also tested in a preliminary fashion. While a rating cannot, from these preliminary tests, assigned to these two dentifrices, the results did show that BRAND W is quite abrasive and is comparable to BRAND Y SMOKER'S toothpaste, while BRAND Z is comparable to BRAND X. It appears, therefore, that the toothpaste of this invention lies between these two extremes of abrasivity, as judged by surface roughening of dentin. Since the present toothpaste also removes plaque and tartar (calculus), and Brands X and Z do not remove either tartar or plaque, the toothpaste of this invention can be judged as superior overall.

EXAMPLE 6

Abrasion Evaluation

SEM evaluation was performed to determine the abrasion effects of the toothpaste of this invention in comparison with BRAND W and BRAND Z, in CompGard restoration and enamel. Seven Class V composite restorations were prepared by acid etching the enamel of Class V preparations for 60 seconds, using a phosphoric acid gel. Each acid-etched tooth was thoroughly rinsed for 30 seconds, using tap water, and was then air dried. Teeth were restored using a commercially available microfill restorative, according to the manufacturer's instructions. Each restoration was finished using 3M Sof-Lex disks (medium, fine and superfine).

Each dentifrice was applied to a restored tooth surface using a prophy cup and a slow speed handpiece. After application for thirty seconds, samples were thoroughly rinsed and air dried. In addition, each dentifrice was diluted 1:1 with tap water to form a slurry. Each slurry was applied to the surface of a second restored tooth using a prophy cup and a slow speed handpiece. Each restored tooth was polished for three (3) ten (10) second intervals and thoroughly rinsed with tap water between each application.

SEM evaluation was also performed to determine the effects of polishing microfilled composite restorations and enamel with a prophylaxis paste after cause prophylaxis with Pert-X. Two Class V microfilled composite restorations were prepared and polished as previously described. After final polish with superfine 3M disks, both restored teeth were given a rough prophylaxis using a cause prophy paste and prophy cup on a slow speed handpiece. After rough prophylaxis, one of the restored teeth was given a final prophylaxis using a prophylaxis paste.

After final treatment, samples were vacuum desiccated and sputter coated with gold. Samples were examined in an AMR-100 SEM at 20 kv accelerating potential and 0° tilt. All SEM photomicrographs were taken at 1000× magnification.

The results of these evaluations indicate the following:

(1) Final polish with each undiluted toothpaste proved to degrade the surface when compared to the surface which was polished only with Sof-Lex disks. The use of each toothpaste from the tube marred the surface more severely than did the toothpastes diluted 1:1 with tap water.

(2) While there was a definite effect of each undiluted toothpaste on the surface finish, BRAND W appeared to be the most harmful, and there was little difference if any between BRAND Z and applicants' toothpaste. The harmful effects of roughening the surface was most notable on the enamel surface rather than on the composite.

(3) The adverse effect of the diluted dentifrices on surface finish was much less pronounced than it was when applying the dentifrices without dilution with water. This is to be expected, since less heat would be generated in the diluted form and far less abrasive material was present. Little or no difference could be detected between the dentifrices when used in the 1:1 diluted form.

(4) The rough prophylaxis paste caused significant scratching which macroscopically appeared as a dull surface on both the enamel and composite. Final prophylaxis with the prophylaxis paste significantly improved both the macroscopic and microscopic surface finish of both the enamel and especially the composite.

EXAMPLE 7

In Vitro Abrasivity

The studies reported herein were conducted on toothpaste marked as sample Toothpaste A and Toothpaste B (See Example 4 above). It will be recalled that Toothpaste B is that of Example 1 and contained aluminum oxide in an amount of about 7% by weight of the toothpaste, while Toothpaste A contained no aluminum oxide as well as no sodium citrate, citric acid or papain.

Relative dental abrasivity (RDA) tests conducted by approved ADA methodology (Hefferan, John, J. Dent. Res. 55:563-573) were performed by the Oral Health Research Institute, University of Indiana. The RDA test measures removal of enamel and not surface finish.

Toothpaste A was found to be 50% as abrasive as the ADA reference material, while Toothpaste B was found to be 80-90% as abrasive as the ADA reference material. ADA reference material represents a cross-section of commercial toothpastes.

Therefore, Toothpaste A is of the order of half of the abrasivity of most commercial dentifrices while Toothpaste B is equivalent in relative abrasivity to most commercial toothpastes.

EXAMPLE 8

In order to assess surface finish after brushings, the labial aspect of extracted incisors and bicuspids were mounted in acrylic blocks and placed in a toothbrushing machine equipped with Oral B #30 toothbrushes. A two pound load was placed on each brush by counterweights. Six months simulated brushing was accomplished through the following assumptions:

15 strokes per day times 7 days times 26 weeks=2730 strokes, corresponding to daily brushing for six months.

Dentifrices included Toothpastes "A" and "B", (See Example 7) a positive control of BRAND X, and a negative control of tap water.

The brushes were cleaned after 60 strokes. Toothpaste was supplied as needed during each 60 stroke cycle to keep the teeth covered with dentifrice. The entire apparatus was cleaned after each 300 cycles.

Following brushing, the samples were rinsed in tap water and were then wrapped is tissue to prevent marring of the work surface prior to SEM examination. At examination, the tissue stuck to the surfaces of teeth brushed with Toothpaste B, but not to any of the other surface brushed with other dentifrices.

Addition silicone (Xantopren) replicas and "Stycast" epoxy positive models of the acrylic/tooth surfaces were made prior to and following the brushing regimen. SEM photographs were taken in the backscattered mode at 50×, which was found to provide adequate resolution of the dentine/enamel and acrylic mounting material. The photographs were examined by four observers (two dentists, one hygienist, and one materials scientist). The panel ranked the change between pre- and post-brushing for material removal (wear), and the change in surface morphology in the surfaces presented, and they were unanimous in their ranking.

Least change—tap water
Most change—BRAND X
Intermediate—toothpastes "A" and "B" although B was felt to have slightly more wear than A. This is a subjective confirmation to the RDA results reported above.

All three dentifrices appeared to polish the surfaces of dentin and enamel. The consensus showed the rankings to be A<B<BRAND X. However, none of the dentifrices appeared to severely groove the enamel or dentine. Faint, fine grooving may be discerned, however, in the brushed surfaces with all three dentifrices. From previous abrasion studies, BRAND X appears to be one of the least abrasive of commercial toothpastes; therefore, both toothpastes A and B seem to be quite acceptable from an abrasion and polishing point of view.

Toothpaste B was thus found to be more abrasive than Toothpaste A but within the accepted range for commercial dentifrices.

Toothpaste B appears to be at least equivalent in surface polishing to Toothpaste A and produces less morphological changes than BRAND X.

EXAMPLE 9

Stain Removal

As shown in Example 4, a stained pellicle (coffee and tea) cleaning study was conducted on Toothpastes A and B by the Oral Research Health Center, University of Indiana. It clearly showed that Toothpaste B was significantly superior to Toothpaste A in stain removal.

Toothpaste B is significantly superior to Toothpaste A in regard to stain removal.

EXAMPLE 10

Abrasivity on Polished Composite Dental Resins

Commercially available toothpastes and their effect on the surface of polished composite resins was evaluated. The resin was a tooth-colored, glass-filled plastic polymer used as a restorative (filling) material for anterior and posterior teeth. The toothpastes being compared were Toothpaste B (that of Example 1) and brands D, E, F, G, H, and I.

The research method was to polish three types of composite resins to a clinically smooth and lustrous surface using a series of aluminum oxide polishing discs from coarse to superfine. Then each sample of polished composite was compared for surface smoothness by taking photos at 750× and 1500× using a Scanning Electron Microscope. These photos were ranked for smoothness of surface by two evaluators. Additional samples were prepared and polished in the same manner and then polished with a rotating rubber dental prophylaxis cup for one minute with each of the toothpastes. Scanning Electron Microscope photographs were taken in the same manner as described and these photographs were ranked ordered.

Evaluation of the data collected showed that all the toothpastes created a roughening of the composite resin surface from the baseline. The surface texture of the composite resin surface when polished with the Toothpaste B was only slightly different than the baseline. Brands D, E, F, G, H, and I, all created a significantly rougher surface from the baseline polish of the composite resin.

The significance of this study is that composite resins have more than doubled in their usage in the past five years for the restoration of teeth in the anterior and posterior regions of the mouth. With this increased usage there is a need to maintain the polished surface of these composite resins. The roughening effect of the teste toothpastes Brands D, E, F, G, H, and I can cause the composite resins to need premature replacement as restorations in the mouth, due to both staining and wear. The toothpaste of the present invention, because of its likeness to the typical professional polishing systems used in dentistry for composite resins, is less abrasive and leaves a significantly smoother surface that will be stain resistant.

When the toothpaste of this invention was given to patients to use clinically to reduce or remove stain from existing composite resin restorations, it was reported by the patients that within three weeks the stain was reduced or no longer present. It is expected that the routine use of the toothpaste of the present invention will maintain the polished, lustrous surface of the composite resin.

As already has been said, such ingredients as the foaming agent, the fluoride source, the sweetener, the biocide and the color are by no means essential. Moreover, the approximate amounts by weight as given in this table are not absolutely essential and variations may be used.

EXAMPLE 11

Fifteen very dirty extracted human teeth were obtained, randomized, and separated into three groups. Each tooth was brushed on either the labial (or buccal) surface or the lingual surface, whichever appeared more dirty and/or contained the most plaque and/or tartar. Each was brushed a total of 50 strokes with an Oral B toothbrush according to the following schedule:
Group I—Brushed with water only
Group II—Brushed with water and the following formula (1:1):

| Ingredients | Percent by Weight |
| --- | --- |
| Dicalcium phosphate | 45.22 |
| Water | 12.96 |
| Sorbitol | 12.08 |
| Glycerin | 13.66 |
| Sodium carrageenan | 0.73 |
| Sodium lauryl sulfate | 0.82 |
| Flavor | 0.82 |
| Sodium saccharin | 0.10 |
| Sodium monofluorophosphate | 0.73 |
| Methyl paraben | 0.07 |
| FD & C Blue #1 | 0.02 |
| Potassium citrate | 2.89 |
| Citric acid | 0.05 |
| Papain | 2.69 |
| Aluminum oxide (1 micron) | 7.16 |
| | 100.00 |

This formula is like the toothpaste of Example 1 with potassium citrate substituted for sodium citrate.

Group III—Brushed with water and the toothpaste of this invention (1:1) (per Example 1).

After brushing, the teeth were water-rinsed and allowed to air-dry. When dry, each group of teeth was carefully inspected. Differences were very obvious, and were as follows:

Group I—Still very dirty. Little or no difference was seen between the brushed and unbrushed surfaces.

Group II—Brushed surfaces were noticeably cleaner. There was and obvious difference in plaque and tartar deposits.

Group III—Brushed surfaces were noticeably cleaner. There was an obvious difference in plaque and tartar obvious.

Group II and III were, in fact, judged to be equivalent in degree of cleaning.

EXAMPLE 12

Pellicle Cleaning Study Specimen Preparation

Bovine permanent central incisors were cut to obtain labial enamel specimens approximately 10 mm$^2$. The enamel specimens were imbedded in an autopolymerizing methacrylate resin so that only the enamel surfaces were exposed. The enamel surfaces were then smooth and polished on a lapidary wheel. They were lightly etched to expedite stain accumulation and adherence.

The specimens were placed on a rotating rod (placed in 37° C. incubator) alternately exposing them the air and to a solution consisting of trypticase soy broth, tea, coffee, mucin, FeCl3, and *Sarcina lutea*.

The staining broth was changed and specimens rinsed once daily for four days. After four days, a darkly-stained pellicle film was apparent on the enamel surface. Specimens were rinsed, allowed to air dry, and refrigerated until use. All products were tested using specimens prepared at the same time.

Scoring and Set Up

The amount of in vitro stain was graded photometrically. Specimens with scores between 16–24 (16 being more darkly stained) were used. On the basis of these scores, the specimens were divided and balanced into 5 groups of 8 specimens each, with each group having the same average baseline score.

Test Procedure

The specimens were mounted on a V-8 mechanical crossbrushing machine equipped with soft nylon-filament (Oral B 40) toothbrushes. Tension on the enamel surface was adjusted to 150 g. The dentifrices were tested as a slurry consisting of 25 grams of dentifrice mixed with 40 ml. of deionized water and the ADA reference material was a slurry consisting of 10 grams of $Ca_2P_2O_7$ mixed with 50 ml. of 0.5% CMC. Specimens were brushed for 800 strokes (4½ minutes). To minimized mechanical variables, two specimens per group were brushed on each of the eight brushing heads. Four different products were used twice on each run, with two tubes of slurry made up for each product. Fresh slurry was made up after four teeth had been run per tube.

Following brushing, specimens were rinsed, blotted dry, and scored again for stain as previously described.

This study was then repeated with a second set of eight specimens in each group.

Calculations

The difference between the pre- and post-brushing stain scores was calculated and the mean and standard error calculated for the reference group in each study.

The cleaning ratio for each of the two reference material groups (one in each study) was assigned a value of 100. The mean decrement for each reference was divided into 100 to obtain a constants value to multiply times each individual decrement within each study. The cleaning ratio of each specimen was then calculated (decrement X constant). The mean and SEM of each dentifrice group (N=16) was calculated using the cleaning ratios.

TABLE V

Raw Data for Cleaning Ratios

| Cleaning Product | ADA | Toothpaste of Example 1 | Crest Tartar Control Tube | Crest Tartar Control Pump | Topol |
| --- | --- | --- | --- | --- | --- |
| Individual Cleaning Ratios for each Individual Brushed Specimen | 93 | 75 | 91 | 94 | 103 |
| | 105 | 116 | 116 | 107 | 65 |
| | 130 | 150 | 66 | 82 | 116 |
| | 115 | 150 | 92 | 163 | 113 |
| | 91 | 130 | 80 | 100 | 134 |
| | 93 | 110 | 91 | 135 | 95 |
| | 98 | 59 | 114 | 139 | 123 |
| | 76 | 142 | 146 | 109 | 48 |
| | 86 | 78 | 126 | 82 | 85 |
| | 100 | 139 | 96 | 74 | 71 |
| | 118 | 65 | 66 | 112 | 102 |
| | 127 | 140 | 68 | 85 | 73 |
| | 97 | 136 | 98 | 88 | 95 |
| | 76 | 106 | 57 | 106 | 69 |
| | 105 | 65 | 54 | 146 | 63 |
| | 71 | 113 | 75 | 129 | 97 |
| $\bar{X}$ Cleaning Ratio for each Product | 100 ± 4 | 111 ± 8 | 90 ± 7 | 109 ± 7 | 91 ± 6 |

TABLE VI

Summary of Dentin Abrasion Data on Products
RELATIVE ABRASIVE VALUES

| Cleaning Specimen No. | Toothpaste of Example 1 | Topol | Crest Tartar Control Tube | Crest Tartar Control Pump |
| --- | --- | --- | --- | --- |
| 1 | 75.33 | 136.11 | 99.99 | 97.59 |
| 2 | 108.30 | 173.98 | 98.84 | 99.77 |
| 3 | 95.64 | 135.93 | 103.33 | 100.37 |
| 4 | 95.08 | 154.75 | 108.55 | 100.70 |
| 5 | 117.68 | 161.13 | 97.00 | 97.32 |
| 6 | 117.56 | 152.88 | 96.26 | 85.40 |

TABLE VI-continued

Summary of Dentin Abrasion Data on Products
RELATIVE ABRASIVE VALUES

| Cleaning Specimen No. | Toothpaste of Example 1 | Topol | Crest Tartar Control Tube | Crest Tartar Control Pump |
|---|---|---|---|---|
| 7 | 121.42 | 136.75 | 99.43 | 98.62 |
| 8 | 94.24 | 145.40 | 87.26 | 86.48 |
| Raw Mean Score | 103.16 | 149.62 | 98.93 | 95.78 |
| ± SEM | 5.60 | 4.85 | 2.17 | 2.19 |
| Self Absorption Correction Factor | 1.08 | 1.07 | 1.17 | 1.14 |
| Corrected Mean Score ± SEM | 111.41 6.05 | 160.09 5.19 | 115.63 2.54 | 109.19 2.50 |

TABLE VII

Summary of Pellicle Cleaning and Dentin Abrasion Data on Four Products Provided by Greenmark, Inc.

| Dentifrice | Pellicle Cleaning | Dentin Abrasion |
|---|---|---|
| Toothpaste of Example 1 | 111 ± 8* ** | 111 ± 6 |
| Crest Tartar Control-Tube | 109 ± 7 | 116 ± 3 |
| ADA Reference Material | 100 ± 4 | 100 |
| Topol | 91 ± .6 | 160 ± 5a |
| Crest Tartar Control-Pump | 90 ± 7 | 109 ± 3 |

*Standard error of the mean
**Values within brackets do not differ significantly (p <0.05) as determined by LSD analysis.
a Value 160 is significantly higher than remaining values.

Tests show clearly that the toothpaste of Example 1 is statistically superior in the Oral Research Health Institute pellicle cleaning test to Topol and Crest Tartar Control-Pump and equivalent to Crest Tartar Control-Tube.

In the Relative Abrasion tests, the toothpaste of this invention was statistically equivalent to the ADA reference material.

EXAMPLE 13

A batch of toothpaste was made identical to that of Example 1 with the exception that citric acid was replaced with acetic acid.

Ten extracted human teeth were divided into two random groups of five each and brushed as in Example 3 using the toothpaste of the present invention as the control.

It was judged that there was essentially no difference between the two groups of teeth which would indicate that it is the citrate ion concentration that is important, not the actual presence of any amount of citric acid.

EXAMPLE 14

A batch of toothpaste was made identical to Example 1 except that flour of pumice, ground to a particle size of approximately 1 micron, was substituted for the aluminum oxide and then tested as in Example 3.

There was a significant difference between the two groups of teeth indicating that the 1 micron aluminum oxide is essential to the action of the toothpaste of this invention.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A toothpaste containing as active ingredients alkali metal citrate in an amount of about 1 to about 3.3% by weight of the toothpaste, citric acid in amounts up to about 3% by weight of the completed toothpaste, to provide a substantially neutral pH for the completed toothpaste, papain in an amount of about 1 to about 4.5% at activity level of 100–145 units/mg, as determined by Milk Clot assay test of the Biddle-Sawyer Group, and fine particle sized aluminum oxide with a particle size of about 1 micron in an amount of about 4 to about 12% by weight of the completed toothpaste.

2. A toothpaste comprising the following basic ingredients:

| Ingredient | % by Weight |
|---|---|
| toothpaste abrasive | 40–50 |
| water | 11–15 |
| humectants | 20–30 |
| thixotropic agent | 0.6–0.8 |
| sodium citrate | 1–3 |
| citric acid | 0–3 |
| papain activity of 100–145 units/mg | 1–4.5 |
| aluminum oxide averaging about 1 micron particle size | 4–12 |

3. The toothpaste of claim 2 containing a foaming agent in an amount of about 0.7 to 0.9% by weight.

4. A toothpaste having approximately the following composition:

| Ingredients | % by Weight |
|---|---|
| Dicalcium phosphate | 45. |
| Water | 13. |
| Sorbitol | 12. |
| Glycerin | 14. |
| Sodium carrageenan | 0.75 |
| Sodium lauryl sulfate | 0.8 |
| Flavor (e.g., Spearmint) | 0.8 |
| Sodium mono fluorophosphate | 0.75 |
| Sweetener (e.g., sodium saccharin) | 0.1 |
| Methyl paraben | 0.1 |
| Color FD & C Blue #1 | 0.03 |
| Sodium citrate | 2.6 |
| Citric acid | 0.07 |
| Papain (activity of 100–145 units/mg) | 2.7 |
| Aluminum oxide (1 micron) | 7.3 |
| | 100.00 |

5. A toothpaste comprising the following basic ingredients:

| Ingredient | % by Weight |
|---|---|
| toothpaste abrasive | 40–50 |
| water | 11–15 |
| humectants | 20–30 |
| thixotropic agent | 0.6–0.8 |
| potassium citrate | 1.1–3.3 |
| citric acid | 0–3 |
| papain activity of 100–145 units/mg | 1–4.5 |
| aluminum oxide averaging about 1 micron particle size | 4–12 | said toothpaste having a pH between 6 and 7.5.

6. The toothpaste of claim 5 containing a foaming agent in an amount of about 0.7 to 0.9% by weight.

7. A toothpaste having approximately the following composition:

| Ingredient | % by Weight |
| --- | --- |
| Dicalcium phosphate | 45. |
| Water | 13. |
| Sorbitol | 12. |
| Glycerin | 14. |
| Sodium carrageenan | 0.7 |
| Sodium lauryl sulfate | 0.8 |
| Flavor (e.g., Spearmint) | 0.7 |
| Sodium mono fluorophosphate | 0.7 |
| Sweetener (e.g., sodium saccharin) | 0.1 |
| Methyl paraben | 0.1 |

-continued

| Ingredient | % by Weight |
| --- | --- |
| Color FD & C Blue #1 | 0.03 |
| Potassium citrate | 2.9 |
| Citric acid | 0.07 |
| Papain (activity of 100–145 units/mg) | 2.7 |
| Aluminum oxide (1 micron) | 7.2 |
| | 100.00 |

8. The toothpaste of claim 1 wherein said alkali metal citrate is sodium citrate.

9. The toothpaste of claim 1 wherein said alkali metal citrate is potassium citrate.

* * * * *